(12) United States Patent
Van Hoecke et al.

(10) Patent No.: US 7,563,472 B2
(45) Date of Patent: Jul. 21, 2009

(54) COMPOSITION FOR REPLACING MILK POWDER

(75) Inventors: Pieter Paul Marc Van Hoecke, Meilegem (BE); Dirk Reimond Provoost, Vilvoorde (BE)

(73) Assignee: Cerestar Holding B.V., Sas van Gent (NL)

( * ) Notice: Subject to any disclaimer, the term of this patent is extended or adjusted under 35 U.S.C. 154(b) by 724 days.

(21) Appl. No.: 10/528,167

(22) PCT Filed: Sep. 17, 2003

(86) PCT No.: PCT/EP03/10337

§ 371 (c)(1),
(2), (4) Date: Apr. 5, 2005

(87) PCT Pub. No.: WO2004/026048

PCT Pub. Date: Apr. 1, 2004

(65) Prior Publication Data

US 2006/0134309 A1 Jun. 22, 2006
US 2007/0275154 A9 Nov. 29, 2007

(30) Foreign Application Priority Data

Sep. 19, 2002 (GB) ................... 0221746.1

(51) Int. Cl.
*A23J 1/12* (2006.01)
*A23K 1/18* (2006.01)

(52) U.S. Cl. ........................ 426/656; 426/2; 426/658; 426/74; 426/807; 426/805

(58) Field of Classification Search ............. 426/74, 426/656, 658, 807, 2, 805
See application file for complete search history.

(56) References Cited

U.S. PATENT DOCUMENTS

| | | | | |
|---|---|---|---|---|
| 3,849,194 A | * | 11/1974 | Armbruster et al. | 127/29 |
| 4,054,677 A | | 10/1977 | Orban | |
| 4,973,488 A | * | 11/1990 | Ernster | 426/580 |
| 6,096,353 A | * | 8/2000 | Meheus et al. | 426/53 |
| 6,176,916 B1 | | 1/2001 | De Sadeleer | |

FOREIGN PATENT DOCUMENTS

| | | | |
|---|---|---|---|
| EP | 0 803 198 | | 10/1997 |
| EP | 0875155 | | 11/1998 |
| GB | 1 519 164 | | 7/1978 |
| WO | WO 00/48474 A | | 8/2000 |
| WO | WO 0048474 | * | 8/2000 |

OTHER PUBLICATIONS

Branen et al. "Food Additives" published 2001, CRC Press, p. 793.*

* cited by examiner

*Primary Examiner*—C. Sayala
(74) *Attorney, Agent, or Firm*—Fitch, Even, Tabin & Flannery

(57) ABSTRACT

The current invention relates to a composition comprising a) from 20 w/w % to 70 w/w % cereal proteins, b) from 25 w/w % to 70 w/w % maltodextrin, c) from 1 w/w % to 20 w/w % amino acids, and d) from 0 w/w % to 20 w/w % minerals, and e) from 0 w/w % to 45 w/w % fat. The composition is prepared according to a process wherein maltodextrin and cereal proteins are mixed and liquid amino acids are added, followed by drying to appropriate dry substance. The composition can be applied in food and feed applications as milk powder replacer.

18 Claims, No Drawings

COMPOSITION FOR REPLACING MILK POWDER

This Application is the National Phase of International Application No. PCT/EP03/10337 filed Sep. 17, 2003, which designated the U.S. and was published under PCT Article 21(2) in English, and this application also claims, via the aforesaid International Application, the foreign priority benefit of and claims the priority from European Application No. EP 0221746.1, filed Sep. 19, 2002, the complete disclosures of which are incorporated herein by reference.

TECHNICAL FIELD

The present invention relates to a composition useful as a protein source for use as milk powder replacer in feed and food applications. Furthermore, it relates to an economic process for preparing said composition.

BACKGROUND OF THE INVENTION

The products of the present invention find application as milk powder replacer. These products can be applied in feed and food products.

In relation to food applications, there is a big concern in finding suitable and cheap products as milk replacers for babies, elderly persons and everybody in need for having appropriate intake of proteins.

In relation to animal feed, there is a big concern in feeding young animals, especially young ruminants however, other animals like pets are not excluded. Young calves, lambs and pigs depend on mother's milk to provide nourishment during the period when the rumen and other digestive functions have not yet developed. Young animals are therefore unable to utilize the feed consumed by adult animals. For calves this period comprises two stages. The first stage is the so-called pre-ruminant stage i.e. when the digestive functions are more akin to those of monogastric animals. During the second stage the rumen is developing but is not yet capable of fully performing the animals needs. Depending on the type of food offered and the intended use of the animals the pre-ruminant stage may be shorter or longer. Because of the high costs and inconvenience of feeding liquid cow's milk, artificial milk replacers have been developed. Milk replacers contain the following ingredients; milk proteins, fat, carbohydrates, vitamins and minerals. Milk proteins generally used are whey proteins and dried skim milk powder manufactured from cow's milk.

The physico-chemical and nutritional characteristics of the milk proteins have been shown to be of such a nature that replacement with other proteins gives rise to a lot of problems. When artificial milk replacers are made the finished product contains a series of components and care should be taken that the mixture has the right dispersibility, or solubility in water. Moreover, care has to be taken that the color, taste and smell are acceptable.

The supply and costs of skinned milk powder make it attractive to try to find other protein sources for pre-ruminant or young ruminant feed purposes, and food purposes. A lot of effort has been spend on trying to find or develop suitable protein sources for example, efforts have been made to develop products starting from soya bean meal, from fish meal, and from microbial sources such as yeasts. It has turned out that the finding of a suitable alternative protein source is not a straightforward process. In particular problems have occurred with the solubility and suspendibility of products, moreover inadequate growth due to the presence of anti-nutritional factors and bad feed conversion has often been observed.

European patent EP 0 479 596 discloses a process for treating sources of vegetable protein and carbohydrate comprising, preparing an aqueous slurry of vegetable proteins and carbohydrates; adjusting the pH of the slurry between 3.5 and 6; pretreating the slurry with a viscosity reducing agent (an enzyme or an anti-oxidant); heating the slurry; cooling and hydrolysing with a hydrolysing agent from a source of alpha-galactosidase.

U.S. Pat. No. 5,138,038 discloses protein partial degradation products obtainable from grain proteins by specific degradation treatment. The products are useful as quality improving agents for various food stuffs, as surface active agents and as dispersing agents for particles.

WO 00/48474 relates to a calf milk replacer composition comprising from 1 to 20 parts by weight of vegetable protein concentrate or isolate, and from 8 to 20 parts by weight of a carbohydrate source together with whey powder and/or delactose whey powder and/or whey protein concentrate, fat and additives. According to the invention it is essential that the carbohydrate source is a combination of processed starch and maltodextrin wherein the maltodextrin is characterized by its DE-value between 10 and 35.

EP 0 446 987 relates to a composition for the preparation of artificial calf milk which composition contains carbohydrates, lactoproteins, vegetable proteins and fat wherein at least part of the vegetable protein consists of soluble wheat protein.

Derwent Abstract of HU 54292 describes a lactic acid rich animal feed stuff substituting milk prepared from dairy products.

From the above references and in the general literature it appears that vegetable proteins are considered as an interesting protein source because they are cheap and available in large quantities.

However, a simple process for preparing a suitable composition completed with free amino acids in liquid form, and minerals is needed.

The current invention provides a composition suitable as milk replacer in food and feed applications and a simplified economic process for preparing said composition is provided as well.

SUMMARY OF THE INVENTION

The present invention discloses a composition comprising a) from 20 w/w % to 70 w/w % cereal proteins, b) from 25 w/w % to 70 w/w % maltodextrin, c) from 1 w/w % to 20 w/w % amino acids, and d) from 0 w/w % to 20 w/w % minerals. It relates to a composition which is further comprising from 1 to 45 w/w % fat. It relates to a composition wherein cereal protein is wheat protein, preferably hydrolysed wheat gluten and/or maltodextrin has a DE of 3 to 10, preferably DE of 5. It further relates to a composition wherein amino acids are lysine, threonine, tryptophane, or mixtures thereof.

The current invention is disclosing a composition that is comprising
 a) From 20 w/w % to 50 w/w % wheat gluten,
 b) From 30 w/w % to 70 w/w % maltodextrin,
 c) From 1 w/w % to 5 w/w % lysine,
 d) From 0.3 w/w % to 5 w/w % threonine,
 e) From 0.05 w/w % to 2 w/w % thryptophane,
 f) From 0 w/w % to 5% w/w % calcium-based salts,
 g) From 0 w/w % to 10 w/w % phosphate-based salts,
 h) From 0 w/w % to 45 w/w % fat and,
 i) From 0 w/w % to 5 w/w % sodium chloride.

The current invention is disclosing a composition that is comprising
  a) From 35 w/w % to 45 w/w % wheat gluten,
  b) From 45 w/w % to 55 w/w % maltodextrin,
  c) From 1 w/w % to 5 w/w % lysine,
  d) From 0.3 w/w % to 5 w/w % threonine,
  e) From 0.05 w/w % to 2 w/w % thryptophane,
  f) From 0 w/w % to 5% w/w % calcium hydroxide,
  g) From 0 w/w % to 10 w/w % salts of phosphoric acid, and
  h) From 0 w/w % to 5 w/w % sodium chloride,
  i) From 0 w/w % to 45 w/w % fat.

The current invention further relates to a process for preparing a composition of cereal proteins, maltodextrins, amino acids, and said process is comprising:
  a) Blending in liquid phase maltodextrin and cereal proteins, preferably wheat gluten,
  b) Increasing dry substance of liquid phase,
  c) Adding amino acids in liquid form for obtaining liquid composition,
  d) Optionally adding water soluble minerals for obtaining completed composition,
  e) Optionally adding fat and homogenizing with liquid or completed composition, and
  f) Drying of liquid composition or completed composition.

The current invention relates to a process wherein the drying of the liquid composition or completed composition is performed in a ringdryer.

The current invention filter relates to a process comprising the following steps:
  a) Hydrolysing wheat gluten for obtaining hydrolysed wheat gluten of degree of hydrolysis (DH) between 3 and 15%,
  b) Hydrolysing starch to maltodextrin of DE of from 3 to 10,
  c) Blending in liquid phase hydrolysed wheat gluten and maltodextrin,
  d) Increasing dry substance of liquid phase to at least 55% w/w,
  e) Adding amino acids in liquid form for obtaining liquid composition,
  f) Optionally adding water soluble minerals for obtaining completed composition,
  g) Optionally adding fat and homogenizing with liquid or completed composition, and
  h) Drying of liquid composition or completed composition.

The current invention further relates to a process which is comprising the following steps:
  a) Hydrolysing wheat gluten for obtaining hydrolysed wheat gluten of degree of hydrolysis (DH) between 3 and 15%,
  b) Hydrolysing starch to maltodextrin of DE of 5,
  c) Blending in liquid phase hydrolysed wheat gluten and maltodextrin,
  d) Increasing dry substance of liquid phase to 60% w/w,
  e) Adding in liquid form lysine, threonine and tryptophane for obtaining liquid composition,
  f) Adding calcium hydroxide, salts of phosphoric acid and sodium chloride for obtaining completed composition,
  g) Optionally adding fat and homogenizing with completed composition, and
  h) Drying of completed composition in ringdryer.

The current invention further relates to the use of a composition comprising a) from 20 w/w % to 70 w/w % cereal proteins, b) from 25 w/w % to 70 w/w % maltodextrin, c) from 1 w/w % to 20 w/w % amino acids, and d) from 0 w/w % to 20 w/w % minerals and e) from 0 w/w % to 45 w/w % fat, for replacing milk powder in food applications or feed applications.

The current invention relates to the use in feed applications suitable for young animals. These young animals can be calves, piglets, lambs or pet.

Furthermore, the current invention discloses a calf milk replacer comprising calf milk replacer ingredients and from 1 to 55% of a composition which is containing a) from 20 w/w % to 70 w/w % cereal proteins, b) from 25 w/w % to 70 w/w % maltodextrin, c) from 1 w/w % to 20 w/w % amino acids, d) from 0 w/w % to 20 w/w % minerals, and e) from 0 w/w % to 45 w/w % fat.

It further relates to a calf milk replacer comprising from 1 to 35% of a composition which is containing a) from 20 w/w % to 70 w/w % cereal proteins, b) from 25 w/w % to 70 w/w % maltodextrin, c) from 1 w/w % to 20 w/w % amino acids, d) from 0 w/w % to 20 w/w % minerals, and e) from 0 w/w % to 45 w/w % fat.

DETAILED DESCRIPTION OF THE INVENTION

The present invention discloses a composition comprising a) from 20 w/w % to 70 w/w % cereal proteins, b) from 25 w/w % to 70 w/w % maltodextrin, c) from 1 w/w % to 20 w/w % amino acids, and d) from 0 w/w % to 20 w/w % minerals.

The cereal protein which is used according to the present invention is selected from the group consisting of wheat, barley, rye, oats, sorghum and corn. Wheat proteins, such as wheat gluten are preferred.

Gluten can be wheat gluten defined as vital wheat gluten, fractions of vital wheat gluten, modified wheat gluten, (partially) hydrolysed wheat gluten and or mixtures thereof. Preferably hydrolysed wheat gluten is applied.

The current invention relates to a composition wherein maltodextrin has a DE of 3 to 10, preferably DE of 5.

Maltodextrins are produced commercially by the controlled acid or enzymatic hydrolysis of starch. A hydrolysis product is characterised by its DE (dextrose equivalent) number. In fact, DE number is a measurement of the percentage of reducing sugars present in the syrup and calculated as dextrose on a dry weight basis.

Maltodextrins are characterised by a DE value between 0.1 to 20. The current invention preferably relates to maltodextrins of DE of 3 to 10, more preferably DE of 5.

It relates to a composition which is further comprising from 1 to 45% w/w fat. The fat can be both of vegetable and animal origin or a mixture of both. Animal fats which can be utilized are beef or pork fat. The vegetable fat that can be used is among others palm oil, coconut oil, or hardened fats, mixtures thereof and the like.

It further relates to a composition wherein amino acids are lysine, threonine, tryptophane or mixtures thereof.

In particular, the composition of the current invention comprises wheat gluten, maltodextrins, amino acids and eventual minerals, and optionally fat up to a sum of 100% w/w in total.

Individual amino acids or a mixture of amino acids are added as free amino acids in liquid form to optimize the amino acid composition available in the wheat gluten component and yet not to jeopardize the nutritional constraints by adding the amino acids in the salt form. The addition of free amino acids avoids the salt overload, and specifically the overload of chloor atoms which might imbalance the nutritional value for feed compositions. Such an addition is done either before or after hydrolysis of wheat gluten.

The hydrolysis of the proteins or protein mixture of the present invention is performed by acid or enzymatic hydrolysis. In case of acid hydrolysis the solution is acidified to a pH below 3 and heated for a sufficient amount of time to hydrolyse the protein. Preferably the hydrolysis is an enzymatic hydrolysis wherein the protein solution is brought to a temperature and pH which are adapted to the type of enzyme used. In general this is indicated by the enzyme supplier.

The hydrolysis is followed by determining the degree of hydrolysation (DH). The hydrolysation is allowed to proceed until a DH of between 3 and 15%.

The enzymes used for the present hydrolysis are hydrolases generally peptidases (proteases). Peptidases are synonymous with peptide hydrolases for the entire group of enzymes that hydrolyse peptide bonds. Two sets of subclasses of peptidases are recognized comprising exopeptidases and endopeptidases. These endopeptidases now include the previously known proteinases. Suitable enzymes include Alkalase™, Neutrase™ etc. It is also possible to add transglutaminase.

The current invention is disclosing a composition that is comprising
  a) From 20 w/w % to 50 w/w % wheat gluten,
  b) From 30 w/w % to 70 w/w % maltodextrin,
  c) From 1 w/w % to 5 w/w % lysine,
  d) From 0.3 w/w % to 5 w/w % threonine,
  e) From 0.05 w/w % to 2 w/w % thryptophane,
  f) From 0 w/w % to 5% w/w % calcium-based salts,
  g) From 0 w/w % to 10 w/w % phosphate-based salts,
  h) From 0 w/w % to 45 w/w % fat, and
  i) From 0 w/w % to 5 w/w % sodium chloride.

Such a composition can be completed by adding vitamins, flavours, emulgators and/or trace elements.

The current invention is disclosing a composition that is comprising
  a) From 35 w/w % to 45 w/w % wheat gluten,
  b) From 45 w/w % to 55 w/w % maltodextrin,
  c) From 1 w/w % to 5 w/w % lysine,
  d) From 0.3 w/w % to 5 w/w % threonine,
  e) From 0.05 w/w % to 2 w/w % thryptophane,
  f) From 0 w/w % to 5% w/w % calcium hydroxide,
  g) From 0 w/w % to 10 w/w % salts of phosphoric acid, and
  h) From 0 w/w % to 5 w/w % sodium chloride, and
  i) From 0 w/w % to 45 w/w % fat.

The current invention further relates to a process for preparing a composition of cereal proteins, maltodextrins, amino acids, and said process is comprising:
  a) Blending in liquid phase maltodextrins and cereal proteins, preferably wheat gluten,
  b) Increasing dry substance of liquid phase,
  c) Adding amino acids in liquid form for obtaining liquid composition,
  d) Optionally adding water soluble minerals for obtaining completed composition,
  e) Optionally adding fat and homogenizing with liquid or completed composition, and
  f) Drying of liquid composition or completed composition.

The sequence of step c) and d) and e) is interchangeable.

The current invention allows obtaining a homogeneous mixture of the components to be co-dried prior to entering the dryer.

The current process allows the blending in liquid form and although the dry substance is increased before adding additional amino acids, the amino acids nevertheless can be added in liquid form and the homogenisation of the mixture is easily reached. There is no problem of incompatibility of powder size etc since everything is added in liquid form whereas inhomogenous mixtures are easily obtained by mixing the solid forms (i.e salts, HCl salts of amino acids) of the amino acids with the other components.

The type of mixing device or homogeniser is not critical as long as they are able to homogenize the mixture completely.

The drying step can be performed with any type of dryer. A ring-dryer, a pneumatic conveying dryer or a spray dryer are all suitable equipments for drying the liquid or completed composition. Preferably the drying of the liquid or completed composition is performed in a ringdryer. The process can be more efficient by applying the ringdryer.

The drying temperature should be limited to avoid a dark colored product in case of co-drying carbohydrates (e.g. maltodextrin and protein (Maillard reaction).

After drying it is necessary to cool the product to avoid brown coloring in case of carbohydrate/protein combination. Any type of cooler can be used, even a pneumatic conveying system is sufficient.

The current invention further relates to a process comprising the following steps:
  a) Hydrolysing wheat gluten for obtaining hydrolysed wheat gluten of degree of hydrolysis (DH) between 3 and 15%,
  b) Hydrolysing starch to maltodextrin of DE of from 3 to 10,
  c) Blending in liquid phase hydrolysed wheat gluten and maltodextrin,
  d) Increasing dry substance of liquid phase to at least 55% w/w,
  e) Adding amino acids in liquid form for obtaining liquid composition,
  f) Optionally adding water soluble minerals for obtaining completed composition,
  g) Optionally adding fat and homogenizing with liquid or completed composition, and
  h) Drying of liquid composition or completed composition.

Hydrolysis of wheat gluten and hydrolysis of starch into maltodextrins can be performed co-currently or sequentially. Both hydrolysed products are then blended for obtaining a homogeneous suspension.

The hydrolysis of wheat gluten is followed by determining the degree of hydrolysation. The hydrolysation is allowed to proceed until a DH of between 3 and 15%. The enzymes used for the present hydrolysis are hydrolases generally peptidases (proteases). Suitable enzymes include Alkalase™, Neutrase™ etc.

The addition of fat and homogenization with liquid or completed composition might be further improved by adding emulgators.

The current invention further relates to a process which is comprising the following steps:
  a) Hydrolysing wheat gluten for obtaining hydrolysed wheat gluten of degree of hydrolysis (DH) between 3 and 15%,
  b) Hydrolysing starch to maltodextrin of DE of 5,
  c) Blending in liquid phase hydrolysed wheat gluten and maltodextrin,
  d) Increasing dry substance of liquid phase to 60% w/w,
  e) Adding in liquid form lysine, threonine and tryptophane for obtaining liquid composition,
  f) Adding calcium hydroxide, salts of phosphoric acid and sodium chloride for obtaining completed composition,
  g) Optionally adding fat and homogenizing while completed composition,
  h) Drying of completed composition.

In the process, step b) can be omitted and maltodextrin of DE=5 which is available as such can be blended with the hydrolysed wheat gluten according to step c) of said process.

The current invention relates to the use of a composition comprising a) from 20 w/w % to 70 w/w % cereal proteins, b) from 25 w/w % to 70 w/w % maltodextrin, c) from 1 w/w % to 20 w/w % amino acids, d) from 0 w/w % to 20 w/w % minerals and e) from 0 w/w % to 45 w/w % fat for replacing milk powder in food applications or feed applications. The current composition can be applied in any food or beverage for replacing milk powder.

In feed applications the composition of the current invention is particular useful for young animals, such as calves, lambs, piglets or pet animals.

Furthermore, the current invention discloses a calf milk replacer comprising calf milk replacer ingredients and from 1 to 55% of a composition which is containing a) from 20 w/w % to 70 w/w % cereal proteins, b) from 25 w/w % to 70 w/w % maltodextrin, c) from 1 w/w % to 20 w/w % amino acids, d) from 0 w/w % to 20 w/w % minerals, and e) from 0 w/w % to 45 w/w % fat.

It further relates to a calf milk replacer comprising from 1 to 35% of a composition which is containing a) from 20 w/w % to 70 w/w % cereal proteins, b) from 25 w/w % to 70 w/w % maltodextrin, c) from 1 w/w % to 20 w/w % amino acids, d) from 0 w/w % to 20 w/w % minerals, and e) from 0 w/w % to 45 w/w % fat.

In general the product of the present invention is used as a raw material, ingredient or carrier for the feed or food industry depending on the type of components which are used.

The product is for example used in feed, feed concentrates or premixes. The product can be used as milk replacer in animal feed for example in pig feed, preferably in starters or prestarters and in calf milk replacers.

The current invention has the following advantages:
The composition is better adapted to the nutritional constraints since salt overloads are avoided and the amino acids are added as free amino acids in liquid form.
simplified process which is not suffering from inhomogenicity.
Addition of amino acids in liquid form is a more economic process
Applying the ringdryer allows a more economic process
The composition is provided as one complete powder containing all ingredients needed for application in feed and food.
Hygroscopicity of existing premixes can be avoided.
Mixing problems due to inhomogenicity of particle size of different powdered ingredients is avoided
Composition can be suspended in water
Vegetable protein source is used as a milk powder replacer.

The current invention is illustrated by the following examples:

EXAMPLE 1

Hydrolysis Wheat Gluten

Gluten was added to water at 58° C., progressively while stirring, to obtain a mix of 30% dry matter. 0.3% Alcalase, and 0.125% Neutrase, (NOVO) were added. Incubation occured, while stirring, at 58° C., at pH 5.7-5.8, during 2h.

2. Starch Hydrolysis

A starch slurry was brought to 30% dry matter. 0.135% Termamyl™ was added and 150 ppm $CaCl_2$. pH was adjusted to 5.9-6.1. The slurry was heated to 105° C. by applying steam injection. The slurry was kept at 105° C. during 20 minutes. The enzymes were inactivated by bringing the slurry to pH 2.8-3.2 with HCl (10%). After 10 minutes the pH was increased to 4.5-5 by applying NaOH (10%) for obtaining maltodextrin.

Blending and Concentration 40 parts of the slurry containing hydrolysed wheat gluten was blended with 49.6 parts of maltodextrin slurry, while stirring. Each slurry had a dry matter content of 30%.

The dry matter was increased from 30% to 56% dry matter in a wiped film evaporator under vacuum at temperature between 50 and 60° C.

The following ingredients were further added:

3.06 parts liquid lysine, 0.95 parts threonine, 0.16 parts trytrophane, 2.7 parts calcium hydroxide and 2.6 parts phosphoric acid were added.

The complete mixture was dried in a ringdryer. Air inlet temperature was 140° C., and air outlet temperature was 80° C. The dry matter of the final product was 95%.

The invention claimed is:

1. A composition comprising:
  a) from 20 w/w % to 70 w/w % cereal proteins,
  b) from 25 w/w % to 70 w/w % maltodextrin having a DE of 3 to 10,
  c) from 1 w/w % to 20 w/w % amino acids, and
  d) from 0 w/w % to 20 w/w % minerals.

2. A composition according to claim 1, wherein said composition further comprises from 1 to 45% w/w fat.

3. A composition according to claim 1, wherein said cereal proteins are wheat proteins.

4. A composition according to claim 1, wherein said amino acids are lysine, threonine, tryptophane, or mixtures thereof.

5. A composition according to claim 1, wherein said composition comprises:
  a) from 20 w/w % to 50 w/w % wheat gluten,
  b) from 30 w/w % to 70 w/w % maltodextrin having a DE of 3 to 10,
  c) from 1 w/w % to 5 w/w % lysine,
  d) from 0.3 w/w % to 5 w/w % threonine,
  e) from 0.05 w/w % to 2 w/w % thryptophane,
  f) from 0 w/w % to 5% w/w % calcium-based salts,
  g) from 0 w/w % to 10 w/w % phosphate-based salts,
  h) from 0 w/w % to 45 w/w % fat, and
  i) from 0 w/w % to 5 w/w % sodium chloride.

6. A composition according to claim 1, wherein said composition comprises:
  a) from 35 w/w % to 45 w/w % wheat gluten,
  b) from 45 w/w % to 55 w/w % maltodextrin having a DE of 3 to 10
  c) from 1 w/w % to 5 w/w % lysine,
  d) from 0.3 w/w % to 5 w/w % threonine,
  e) from 0.05 w/w % to 2 w/w % thryptophane,
  f) from 0 w/w % to 5% w/w % calcium hydroxide,
  g) from 0 w/w % to 10 w/w % salts of phosphoric acid,
  h) from 0 w/w % to 5 w/w % sodium chloride, and
  i) from 0 w/w % to 45 w/w % fat.

7. A process for preparing a composition of cereal protein, maltodextrin, and amino acids, said process comprising:
  a) blending in liquid phase maltodextrin having a DE of 3 to 10, and cereal proteins,
  b) increasing the dry substance of the liquid phase,
  c) adding amino acids in liquid form for obtaining a liquid composition, d) optionally adding water soluble minerals for obtaining a completed composition, e) optionally adding fat and homogenizing with the liquid or completed composition, and f) drying the liquid composition or completed composition.

8. A process according to claim 7, wherein in step f) the liquid or completed composition is dried in a ringdryer.

9. A process according to claim 7, wherein said process comprises the following steps:

a) hydrolyzing wheat gluten for obtaining hydrolysed wheat gluten having a degree of hydrolysis (DH) between 3 and 15%, b) hydrolyzing starch to maltodextrin of DE of from 3 to 10, c) blending in liquid phase hydrolysed wheat gluten and maltodextrin, d) increasing the dry substance of liquid phase to at least 55% w/w, e) adding amino acids in liquid form for obtaining a liquid composition, f) optionally adding water soluble minerals and/or fat for obtaining a completed composition, g) optionally adding fat and homogenizing with the liquid or completed composition, and h) drying the liquid composition or completed composition.

10. A process according to claim 7, said process comprising the following steps:

a) hydrolyzing wheat gluten for obtaining hydrolysed wheat gluten of degree of hydrolysis (DH) between 3 and 15%, b) hydrolyzing starch to maltodextrin of DE of 5, c) blending in liquid phase hydrolysed wheat gluten and maltodextrin, d) increasing dry substance of liquid phase to 60% w/w, e) hydrolyzing in liquid form lysine, threonine and tryptophane for obtaining liquid composition, f) hydrolyzing calcium hydroxide, salts of phosphoric acid and sodium chloride for obtaining a completed composition, g) optionally adding fat and homogenizing with the completed composition, and h) drying the completed composition.

11. A method for replacing milk powder in a food application or in feed application comprising using a composition comprising a) from 20 w/w % to 70 w/w % cereal proteins, b) from 25 w/w % to 70 w/w % maltodextrin having a DE of 3 to 10, c) from 1 w/w % to 20 w/w % amino acids, d) from 0 w/w % to 20 w/w % minerals, and e) from 0 w/w % to 45 w/w % fat, instead of at least a portion of the milk powder when preparing said food application or feed application.

12. The method according to claim 11, wherein said feed applications are suitable for young animals.

13. The method according to claim 12, wherein said young animals are selected from the group consisting of calves, piglets, lambs, and pet.

14. A calf milk replacer comprising as ingredients from 1 to 55% of a composition which is containing a) from 20 w/w % to 70 w/w % cereal proteins, b) from 25 w/w % to 70 w/w % maltodextrin having a DE of 3 to 10, c) from 1 w/w % to 20 w/w % amino acids, d) from 0 w/w % to 20 w/w % minerals, and e) from 0 w/w % to 45 w/w % fat.

15. A calf milk replacer according to claim 14, wherein said calf milk replacer comprises from 1 to 35% of said composition.

16. A composition according to claim 1, wherein said maltodextrin has a DE of 5.

17. A composition according to claim 1, wherein said cereal proteins are hydrolyzed wheat gluten.

18. A composition according to claim 11, wherein said maltodextrin has a DE of 5.

* * * * *